(12) United States Patent
Li Pi Shan et al.

(10) Patent No.: US 10,308,796 B2
(45) Date of Patent: Jun. 4, 2019

(54) COMPOSITION FOR LOW TEMPERATURE USE CONTAINERS

(71) Applicant: Dow Global Technologies LLC, Midland, MI (US)

(72) Inventors: Colin Li Pi Shan, Pearland, TX (US); Raymond L. Laakso, Jr., St. Francisville, LA (US); Eddy I. Garcia-Meitin, Angleton, TX (US)

(73) Assignee: Dow Global Technologies LLC, Midland, MI (US)

( * ) Notice: Subject to any disclaimer, the term of this patent is extended or adjusted under 35 U.S.C. 154(b) by 65 days.

(21) Appl. No.: 15/558,096

(22) PCT Filed: Mar. 7, 2016

(86) PCT No.: PCT/US2016/021132
§ 371 (c)(1),
(2) Date: Sep. 13, 2017

(87) PCT Pub. No.: WO2016/148950
PCT Pub. Date: Sep. 22, 2016

(65) Prior Publication Data
US 2018/0051165 A1    Feb. 22, 2018

Related U.S. Application Data

(60) Provisional application No. 62/132,607, filed on Mar. 13, 2015.

(51) Int. Cl.
| C08L 53/00 | (2006.01) |
| C08L 23/14 | (2006.01) |
| C08L 23/10 | (2006.01) |
| C08L 23/08 | (2006.01) |
| G01N 25/48 | (2006.01) |

(52) U.S. Cl.
CPC .......... C08L 23/14 (2013.01); C08L 23/0815 (2013.01); C08L 23/10 (2013.01); C08L 53/00 (2013.01); *C08F 2500/12* (2013.01); *C08L 2205/035* (2013.01); *C08L 2207/10* (2013.01); *G01N 25/4866* (2013.01)

(58) Field of Classification Search
CPC .......... C08L 23/10; C08L 23/14; C08L 53/00; C08L 2205/035; C08F 2500/12
See application file for complete search history.

(56) References Cited

U.S. PATENT DOCUMENTS

| 3,798,288 A | 3/1974 | McManimie |
| 6,015,854 A | 1/2000 | McCullough, Jr. |
| 6,395,671 B2 | 5/2002 | LaPointe |
| 7,951,882 B2 | 5/2011 | Arriola et al. |
| 8,053,529 B2 | 11/2011 | Carnahan et al. |
| 8,686,087 B2 | 4/2014 | Li Pi Shan et al. |
| 8,716,400 B2 | 5/2014 | Carnahan et al. |
| 2011/0082257 A1* | 4/2011 | Carnahan ............ C08F 297/083 525/88 |
| 2018/0355224 A1* | 12/2018 | Chen ...................... C08L 23/04 |

FOREIGN PATENT DOCUMENTS

EP    911365 A1    4/1999

OTHER PUBLICATIONS

Dharmarajan, Plastics Engineering, 1996, vol. 52, No. 8, p. 33-35.
Yang, "Low Temperature Impact Modifier for Clear Polypropylene Applications"—paper presented at SPE's 64th Annual Conference of the Society of Plastics Engineers held on May 7-11, 2006 in Charlotte, North Carolina.
PCT/US2016/021132, Written Opinion dated Sep. 22, 2016.
PCT/US2016/021132, International Preliminary Report on Patentability dated Sep. 19, 2017.

* cited by examiner

*Primary Examiner* — Jeffrey C Mullis

(57) ABSTRACT

A modifier for forming sub-ambient temperature use containers includes (a) from 20 wt % to 40 wt % of a block composite, the block composite including (i) an ethylene-propylene copolymer, (ii) an isotactic polypropylene polymer, and (iii) a block copolymer, (b) from 40 wt % to 60 wt % of a polyolefin copolymer, the polyolefin copolymer being derived from ethylene and at least one of a $C_3$ to $C_{10}$ alpha-olefin, having a melt index from 100 g/10 min to 1500 g/10 min, according to ASTM D1238 and at 190° C./2.16 kg, and having a density from 0.860 g/cm³ to 0.900 g/cm³, and (c) optionally, from 0 wt % to 30 wt % of at least one of a first additional copolymer that has a refractive index from 1.490 to 1.510 and a second additional copolymer that is miscible with polypropylene.

10 Claims, 4 Drawing Sheets

Comparative Example B

Comparative Example C

Working Example 1

Working Example 2

Working Example 3

COMPOSITION FOR LOW TEMPERATURE USE CONTAINERS

FIELD

Embodiments relate to modifiers for use in compositions for forming high clarity-low temperature use containers such as freezer containers.

BACKGROUND

Polyolefin based materials for forming freezer containers for use at low temperatures (i.e., below 0° C.), that still have high clarity (i.e., greater than 95% clarity), may be challenging. For example, the use of propylene-based random copolymers (RCP) or propylene-based impact copolymers (ICP) that have been impact-modified with elastomers have been proposed. However, the random copolymers may provide the desirable toughness and clarity for many applications, but may suffer from relatively poor impact properties at lower temperatures in comparison to polypropylene impact copolymers. Further, the impact-modified copolymers may suffer from relatively poor clarity in comparison to the random copolymers. Accordingly, a composition is sought that can provide both toughness and clarity even at low temperatures.

SUMMARY

Embodiments may be realized by providing a composition for forming a sub-ambient temperature use container, the composition including from 12 wt % to 30 wt % of a modifier and from 70 wt % to 88 wt % of a propylene polymer base that has a melt flow rate from 2 g/10 min to 100 g/10 min, according to ASTM D 1238 and at 230° C./2.16 kg. The modifier includes (a) from 20 wt % to 40 wt % of a block composite, based on a total weight of the modifier, the block composite including (i) an ethylene-propylene copolymer, (ii) an isotactic polypropylene polymer, and (iii) a block copolymer including an ethylene propylene soft block that has a same composition as the ethylene propylene polymer and an isotactic polypropylene hard block that has a same composition as the isotactic polypropylene polymer, the soft block comprising from 50 wt % to 80 wt % of ethylene based on a total weight of the soft block, and the block copolymer including from 20 wt % to 50 wt % of the hard block, based on the total weight of the block copolymer, (b) from 40 wt % to 60 wt % of a polyolefin copolymer, based on a total weight of the modifier, the polyolefin copolymer being derived from ethylene and at least one of a $C_3$ to $C_{10}$ alpha-olefin, and the polyolefin copolymer having a melt index from 100 g/10 min to 1500 g/10 min, according to ASTM D1238 and at 190° C./2.16 kg, and a density from 0.860 g/cm$^3$ to 0.900 g/cm$^3$, and (c) optionally, from 0 wt % to 30 wt % of at least one of a first additional copolymer that has a refractive index from 1.490 to 1.510 and a second additional copolymer that is miscible with polypropylene, which second additional copolymer is derived from propylene and at least one of ethylene and butene.

BRIEF DESCRIPTION OF THE DRAWINGS

Features of the embodiments will become more apparent to those of ordinary skill in the art with reference to the attached figures, in which.

DETAILED DESCRIPTION

Figure 1:
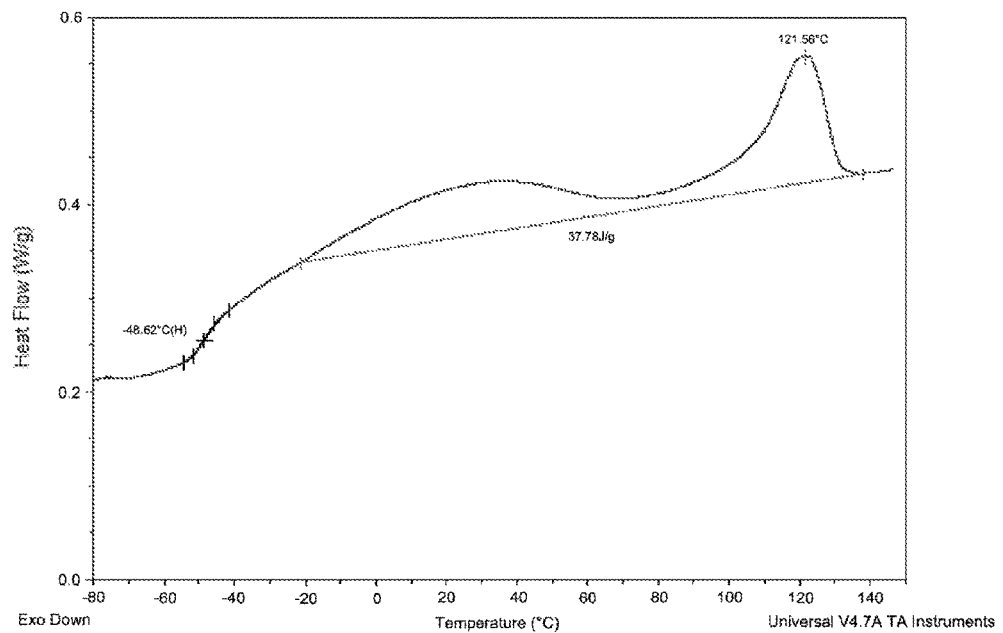
FIG. 1 illustrates a DSC melting point temperature profile for the Block Composite used in the First and Second Modifiers of Working Examples 1 to 6.
Figure 2A:
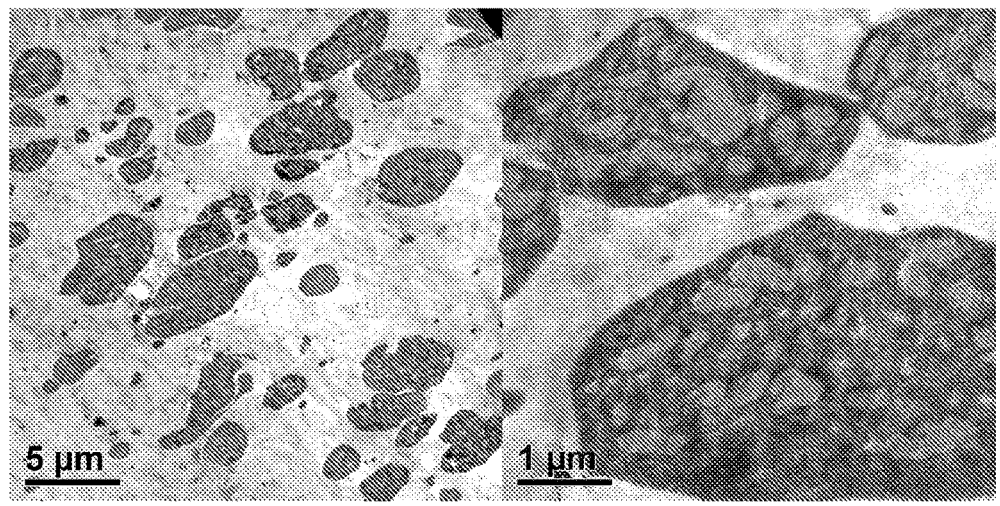
FIG. 2A illustrates the morphology of Comparative Example B at 5 µm and 1 µm.
Figure 2B:
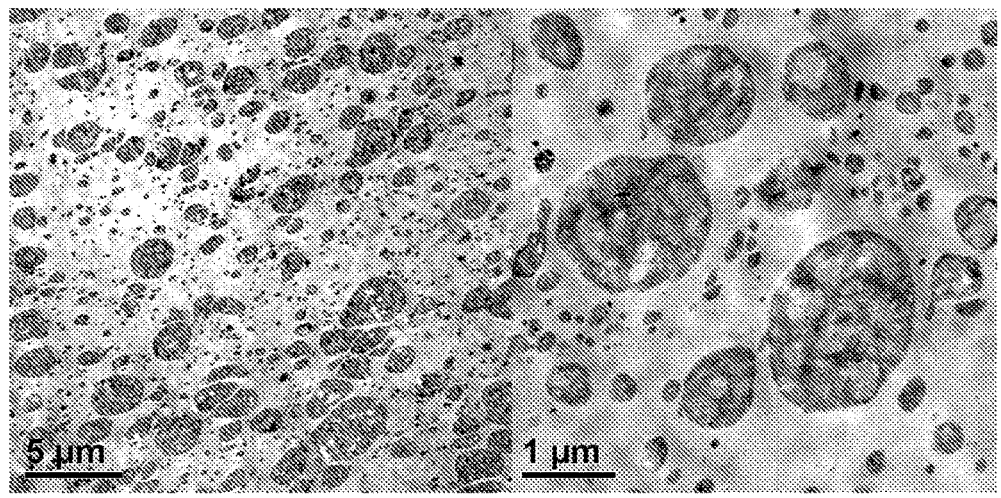
FIG. 2B illustrates the morphology of Comparative Example C at 5 µm and 1 µm.
Figure 2C:
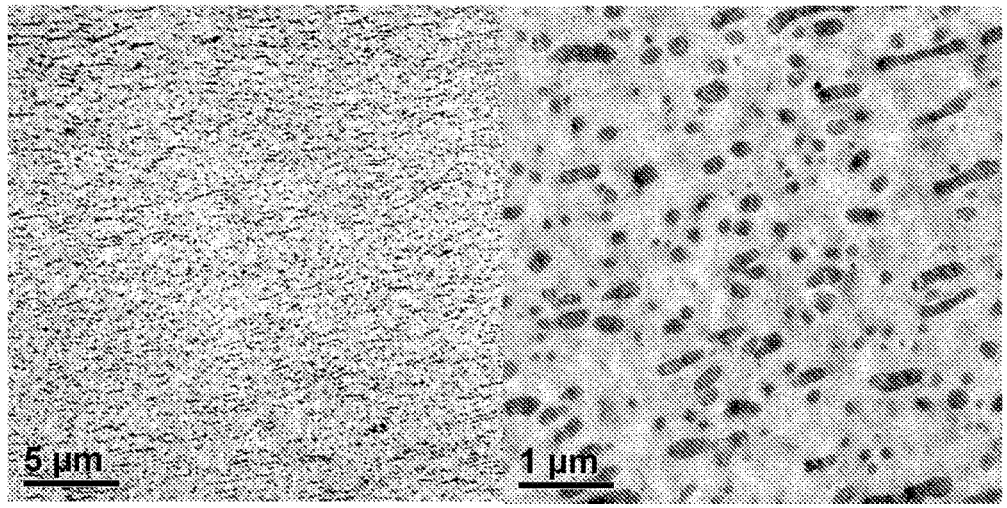
FIG. 2C illustrates the morphology of Working Example 1 at 5 µm and 1 µm.
Figure 2D:
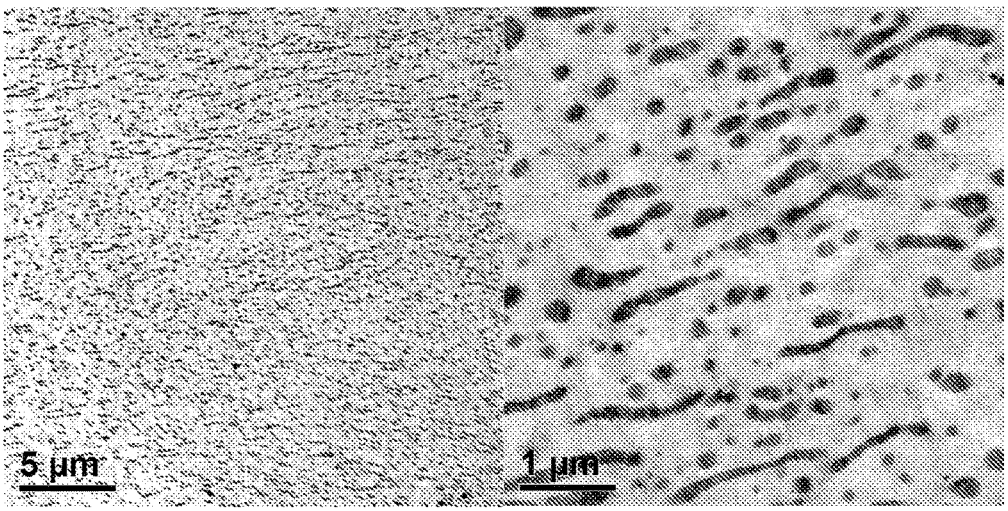
FIG. 2D illustrates the morphology of Working Example 2 at 5 µm and 1 µm.
Figure 2E:
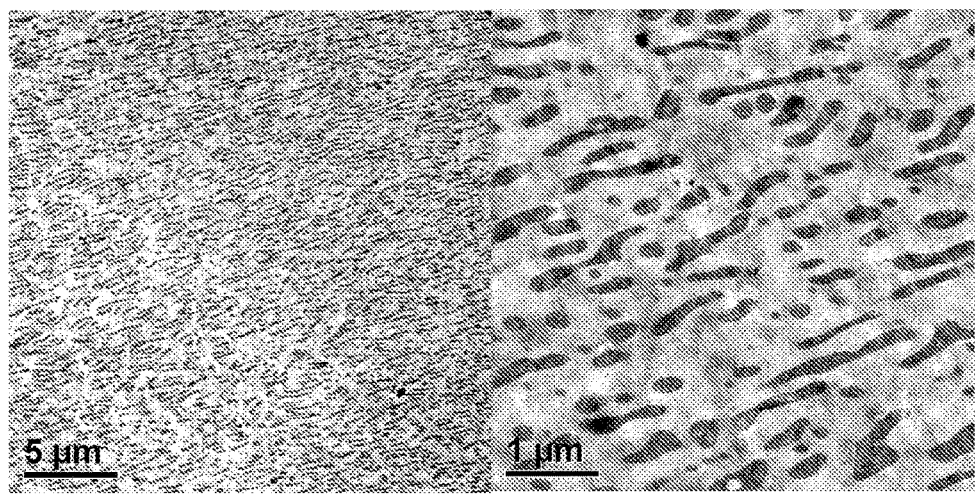
FIG. 2E illustrates the morphology of Working Example 3 at 5 µm and 1 µm.

Clear optics may be challenging when blending ethylene-based elastomers in polypropylene. For example, certain elastomers significantly lower the modulus and clarity of polypropylene. As such, to obtain clear compositions, refractive index matching of the materials have been proposed, e.g., by reducing the rubber domain size to avoid the scattering of the visible wavelengths of light. However, an approach that relies only on refractive index matching of elastomers with polypropylene, has the disadvantage of being restricted to the use of plastomers (such as plastomers having a density greater than 0.900 g/cm$^3$), which may provide lower impact properties especially at lower temperatures. Accordingly, a new compatibilization approach is proposed that replies on particle sizing via compatibilization of non-refractive index matched elastomers with polypropylene, this allows for the expanded use of elastomers having a density from 0.850 g/cm$^3$ to 0.900 cm$^3$ (e.g., 0.850 g/cm$^3$ to 0.890 cm$^3$ and/or 0.850 g/cm$^3$ to 0.870 g/cm$^3$) that have relatively better impact properties at lower temperatures (such as have a relatively lower glass transition temperature).

According to embodiments, a modifier for use with a propylene polymer base to form compositions for forming high clarity-low temperature use containers such as freezer containers has been proposed. The modifier is able to enhance toughness at low temperatures (i.e., below 0° C.) while still forming a high clarity (i.e., greater than 95% clarity) container. With respect to the modifier, impact efficiency of an elastomeric modifier is directly related to crystallinity of the modifier and dispersion of the individual elastomer domains into a polypropylene matrix. Further, conventionally, the dispersion of an elastomer into polypropylene may be challenged in view of, e.g., the melt-mixing process and compatibility. Accordingly, embodiments relate to a modifier that combines an impact resistance provider for enhancing toughness at low temperatures, a high melt flow provider for enabling good melt-mixing, and optionally a clarity provider that has refractive index from 1.490 to 1.510 (e.g., so as to be near the refractive index of a polypropylene homopolymer) and/or is miscible with polypropylene (e.g., a material that is known to one of ordinary skill in the art as being miscible with a polypropylene homopolymer). For example, the modifier may be provided in pre-blended form as a single component (e.g., in pellet form) and added into an existing process that uses at least a propylene polymer base for forming a container such as a freezer container. As would be understood by a person of ordinary skill in the art, the modifier may be added as separate components to the propylene polymer base, even though that may not be commercially efficient and/or preferred.

Terms

"Composition" and like terms mean a mixture or blend of two or more components. For example, one composition is the combination of a random or propylene based polymer and a block composite.

"Blend," "polymer blend" and like terms mean a blend of two or more polymers. Such a blend may or may not be miscible. Such a blend may or may not be phase separated. Such a blend may or may not contain one or more domain configurations, as determined from transmission electron spectroscopy, light scattering, x-ray scattering, and any other method known in the art.

"Polymer" means a compound prepared by polymerizing monomers, whether of the same or a different type. The generic term polymer, thus, embraces the term homopolymer, usually employed to refer to polymers prepared from only one type of monomer, and the term interpolymer as defined below. The term polymer also embraces all forms of interpolymers, e.g., random, block, homogeneous, heterogeneous, etc. The terms "ethylene/alpha-olefin polymer" and "propylene/alpha-olefin polymer" are indicative of interpolymers as described below.

"Interpolymer" and "copolymer" mean a polymer prepared by the polymerization of at least two different types of monomers. These generic terms include both classical copolymers, i.e., polymers prepared from two different types of monomers, and polymers prepared from more than two different types of monomers, e.g., terpolymers, tetrapolymers, etc.

"Propylene-based polymer," and like terms mean a polymer that comprises a majority weight percent polymerized propylene monomer (based on the total amount of polymerizable monomers), and optionally comprises at least one polymerized comonomer different from propylene so as to form a propylene-based interpolymer. For example, when the propylene-based polymer is a copolymer, the amount of propylene is greater than 50 wt %, based on the total weight of the copolymer. "Units derived from propylene" and like terms mean the units of a polymer that formed from the polymerization of propylene monomers. "Units derived from α-olefin" and like terms mean the units of a polymer that formed from the polymerization of α-olefin monomers, in particular at least one of a $C_{3-10}$ α-olefin. In contrast, "Ethylene-based polymer" and like terms mean a polymer that comprises a majority weight percent polymerized ethylene monomer (based on the total weight of polymerizable monomers), and optionally may comprise at least one polymerized comonomer different from ethylene so as to form an ethylene-based interpolymer. For example, with the ethylene-based polymer is a copolymer, the amount of ethylene is greater than 50 wt %, based on the total weight to the copolymer.

"Random propylene-based copolymer" and like terms mean a propylene/α-olefin interpolymer in which the units derived from the α-olefin monomer are randomly distributed across the polymer chain, as opposed to distributed across the polymer chain in an alternating, periodic, or block pattern. An exemplary random propylene-based interpolymer, is a random propylene-based copolymer. In contrast, "homogeneous propylene-based interpolymer" and like terms mean a propylene/α-olefin interpolymer in which the units derived from the α-olefin monomer are randomly and approximately evenly distributed across the polymer chains of the bulk polymer.

"Impact modified propylene-based copolymer" and the like terms mean a propylene-based polymer composition that has been impact-modified such that the composition's notched Izod impact strength at room temperature or below is maintained or increased as compared to said given composition's notched Izod impact strength at the same temperature without the added impact modifier.

"Block composite" and the like terms mean a composite that includes a soft copolymer, a hard polymer, and a block copolymer having a soft segment/block and a hard segment/block, wherein the hard segment of the block copolymer is essentially the same composition as the hard polymer in the block composite and the soft segment of the block copolymer is essentially the same composition as the soft copolymer of the block composite. In particular, the block composite includes a hard polymer that includes polypropylene and a soft polymer that includes ethylene (an ethylene-propylene polymer).

"Block copolymer" refers to a polymer comprising two or more chemically distinct regions or segments (referred to as "blocks") joined in a linear manner, that is, a polymer comprising chemically differentiated units that are joined (covalently bonded) end-to-end with respect to polymerized functionality (e.g., polymerized propylenic functionality), rather than in pendent or grafted fashion. Block copolymers comprise sequences ("blocks") of the same monomer unit, covalently bound to sequences of unlike type. The blocks can be connected in a variety of ways, such as A-B in diblock and A-B-A triblock structures, where A represents one block and B represents a different block. In a multi-block copolymer, A and B can be connected in a number of different ways and be repeated multiply. It may further comprise additional blocks of different type. Multi-block copolymers may be linear multi-block, multi-block star polymers (in which all blocks bond to the same atom or chemical moiety) or comb-like polymers where the B blocks are attached at one end to an A backbone. The block copolymers can be linear or branched. With respect to the block copolymers, the blocks may differ in the amount of comonomer incorporated therein. The blocks may also differ in the type of comonomer, density, the amount of crystallinity, the crystallite size attributable to a polymer of such composition, the type or degree of tacticity (isotactic or syndiotactic), regio-regularity or regio-irregularity, the amount of branching, including long chain branching or hyper-branching, the homogeneity, or any other chemical or physical property. The block copolymers are characterized by unique distributions of polymer polydispersity (PDI or Mw/Mn), block length distribution, and/or block number distribution, e.g., due to the effect of the shuttling agent(s) in combination with the catalyst(s).

"Hard" segments/blocks refer to highly crystalline blocks of polymerized units. The term "Soft" segments/blocks refer to amorphous, substantially amorphous, or elastomeric blocks of polymerized units. "Crystalline" refers to a polymer or polymer block that possesses a first order transition or crystalline melting point (Tm) as determined by differential scanning calorimetry (DSC) or equivalent technique. The term may be used interchangeably with the term "semi-crystalline". The term "crystallizable" refers to a monomer that can polymerize such that the resulting polymer is crystalline. Crystalline propylene polymers may have, but are not limited to, densities of 0.88 g/cc to 0.91 g/cc and melting points of 100° C. to 170° C. "Amorphous" refers to a polymer lacking a crystalline melting point as determined by differential scanning calorimetry (DSC) or equivalent technique.

"Isotactic" is defined as polymer repeat units having at least 70 percent isotactic pentads as determined by $^{13}$C-NMR analysis. "Highly isotactic" is defined as polymers having at least 90 percent isotactic pentads.

Composition

According to embodiments, a composition for forming high clarity-low temperature use containers that includes at least a propylene polymer base and a modifier, and to containers/films formed using the composition thereof. By high clarity-low temperature use container it is meant a container that is formed using a composition that forms a film that is relatively clear with a clarity of at least 95% (e.g., at a thickness of less than 5.0 mm) and exhibits an Izod impact of at least 5 kJ/m$^2$ at a low temperature of −20° C. For example the Izod impact at −20° C. may be from 5 kJ/m$^2$ to 75 kJ/m$^2$, 5 kJ/m$^2$ to 55 kJ/m$^2$, 5 kJ/m$^2$ to 45 kJ/m$^2$, 5 kJ/m$^2$ to 40 kJ/m$^2$, 6 kJ/m$^2$ to 35 kJ/m$^2$, and/or 9 kJ/m$^2$ to 35 kJ/m$^2$. The film for forming the container has a thickness of less than 5.0 mm, less than 4.0 mm, and/or less than 3.0 mm. For example, the thickness may be from 0.1 mm to 4.5 mm, 0.2 mm to 4.0, 0.5 mm to 3.0 mm, and/or 0.5 mm to 2.0 mm.

The composition includes from 12 wt % to 30 wt % of the modifier, based on the total weight of the composition. For example, the amount of the modifier may be greater than 15 wt % and up to 30 wt %, from 18 wt % to 28 wt %, from 19 wt % to 25 wt %, and/or from 18 wt % to 22 wt %, based on the total weight of the composition. The block composite, the polyolefin copolymer, and optionally the additional copolymer of the modifier may be pre-blended prior to blending the modifier with propylene polymer base such that the composition includes the modifier finely dispersed in polypropylene. In another exemplary embodiment, the components of the modifier blend may be individually added at the time of preparation of the article, by feeding the propylene polymer base along with the modifier blend components together into an extruder in one-step to form a modified propylene. In another exemplary embodiment, the modified propylene may be prepared by melt blending all of the individual components of the modifier blend along with the propylene polymer base together and then pelletized for a ready-to-feed modified propylene. This pelletized modified propylene may then be fed directly into a process, e.g., to for an article by injection molding.

The modifier includes from 20 wt % to 40 wt % (e.g., 25 wt % to 35 wt % and/or 28 wt % to 32 wt %) a block composite that includes a block copolymer. The block composite may include one or more block composites. The modifier further includes from 40 wt % to 60 wt % (e.g., 45 wt % to 55 wt % and/or 48 wt % to 52 wt %) of a polyolefin copolymer that has a relatively high melt flow rate and a relatively low density. The polyolefin copolymer may include one or more polyolefin copolymers having the relatively high melt flow rate and the relatively low density. The modifier may optionally include from 0 wt % to 30 wt % (e.g., 10 wt % to 30 wt %, 15 wt % to 25 wt %, and/or 18 wt % to 22 wt %) of at least one additional copolymer. The additional copolymer may have a refractive index similar to that of a polypropylene homopolymer, in particular a refractive index from 1.490 to 1.510 and/or the additional copolymer may be miscible with polypropylene (and is derived from propylene and ethylene and/or butene). The additional copolymer may include one more copolymers having the refractive index similar to that of a polypropylene homopolymer.

With respect to the composition, without intending to be bound by this theory, the blend of the propylene polymer base (e.g., such as a polypropylene homopolymer) and the block copolymer that has a continuous polypropylene phase would result in relatively smaller and discrete rubber domains in comparison to a simple polypropylene/elastomer blend. If the rubber domain sizes are smaller than the wavelengths of visible light (400-700 nm), less scattering of the light would occur, and the polymer/resultant article would maintain clarity. Further, the block copolymer would compatibilize rubber such that the propylene polymer base could be considered impact-modified with improved toughness at low temperatures such as the temperature inside a typical freezer. Accordingly, the resultant composition would be have improved impact modification and while still providing light transmittance similar to that which is realized with a polypropylene homopolymer. For example, the modifier may have the features of being readily compatible and dispersible in polypropylene, remains clear in polypropylene, and results in a composition adapted to form an article that provides sufficient impact toughness at freezer temperatures.

For example, a film formed using the composition of the modifier and the propylene polymer base may exhibit an average Izod at −20° C. that is improved over a film (having the same thickness and formed under the same conditions) formed using only the same propylene polymer base (such as a clarified polypropylene random copolymer and/or a polypropylene homopolymer) and/or a polypropylene impact copolymer. For example, when the composition includes 25 wt % of the modifier the average Izod at −20° C. may be improved by a factor of at least ten times in comparison to when only a clarified polypropylene random copolymer is used, and at least three times in comparison to when only a polypropylene impact copolymer is used. When the composition includes 20 wt % of the modifier, the average Izod at −20° C. may be improved by a factor of at least six times in comparison to when only a clarified polypropylene random copolymer is used, and at least 1.2 times in comparison to when only a polypropylene impact copolymer is used. When the composition includes 15 wt % of the modifier, the average Izod at −20° C. may be improved by a factor of at least three times in comparison to when only a clarified polypropylene random copolymer is used. Accordingly, an improvement with respect to average Izod at −20° C. may be realized when the composition includes the modifier.

A film formed using the composition of the modifier and the propylene polymer base may exhibit a clarity at least as good as a film (having the same thickness and formed under the same conditions) formed using only the propylene polymer base (such as a clarified polypropylene random copolymer). Accordingly, when the modifier is used, a clarity similar to that of a clarified polypropylene random copolymer may be realized. Clarity may be improved for a polypropylene impact copolymer.

A film formed using the composition of the modifier and the propylene polymer base may exhibit a percent haze that is improved by a factor of at least three over a film (having the same thickness and formed under the same conditions) formed using only a polypropylene impact copolymer. When only a clarified polypropylene random copolymer is used to form the comparative film, the percent haze may be similar (e.g., within a range of ±20%).

A film formed using the composition of the modifier and the propylene polymer base may exhibit a percent transmittance that is improved over a film (having the same thickness and formed under the same conditions) formed using only a polypropylene impact copolymer. When only a clarified polypropylene random copolymer is used to form the comparative film, the percent transmittance may be similar (e.g., within a range of ±15%).

A film formed using the composition of the modifier and the propylene polymer base may exhibit a clarity at least as good as a film (having the same thickness and formed under the same conditions) formed using only a clarified polypropylene random copolymer. When only is polypropylene impact copolymer is used to form the comparative film, the clarity may be improved by at least a factor of at least ten (i.e., at least ten times better).

The polymer blends may be used to prepare containers with known polymer processes such as extrusion (e.g., sheet extrusion and profile extrusion); molding (e.g., injection molding, rotational molding, and blow molding); and blown film and cast film processes. For example, in general, extrusion is a process by which a polymer is propelled continuously along a screw through regions of high temperature and pressure where it is melted and compacted, and finally forced through a die. The extruder may be a single screw extruder, a multiple screw extruder, a disk extruder or a ram extruder. The die may be a film die, blown film die, sheet die, pipe die, tubing die or profile extrusion die. Injection molding is used for manufacturing a variety of plastic parts for various applications. Typically, injection molding is a process by which a polymer is melted and injected at high pressure into a mold, which is the inverse of the desired shape, to form parts of the desired shape and size. The mold can be made from metal, such as steel and aluminum. Molding is generally a process by which a polymer is melted and led into a mold, which is the inverse of the desired shape, to form parts of the desired shape and size. Molding may be pressureless or pressure-assisted. In exemplary embodiments, the containers are prepared using injection molding.

The temperature of forming the polymer blend of the modifier with the propylene polymer base may be above the melting temperature of the propylene polymer base. For example, the temperature may be from 150° C. to 250° C. and/or from 200° C. to 225° C., in order to form a homogeneous melt blend. The temperature for forming the modifier, when pre-blended, may be from 150° C. to 200° C. For example, the temperature for pre-blending the modifier may be lower than the temperature for form the polymer blend with the modifier and the propylene polymer base. The polymer blend with the modifier and the propylene polymer base may have a relatively low viscosity blend (compared to traditional modifiers in polypropylene), may operate at a lower temperature, may operate at a lower cycle time, may provide improved uniformity in a resultant part, and/or may provide better homogenous blend with improved balance of clarity and impact properties.

Block Composite

In embodiments, the block composite includes (i) an ethylene-propylene copolymer (also referred to as a soft polymer), (ii) an isotactic polypropylene polymer (also referred to as a hard polymer), and (iii) a block copolymer including an ethylene propylene block (also referred to as an EP soft block) that has a same composition as the ethylene propylene polymer and an isotactic polypropylene block (also referred to as an iPP hard block) that has a same composition as the isotactic polypropylene polymer. With respect to the block copolymer, the soft block comprises from 50 wt % to 80 wt % (e.g., 55 wt % to 75 wt %, 60 wt % to 70 wt %, and/or 63 wt % to 68 wt %) of ethylene based on a total weight of the soft block, with the remainder in the soft block being propylene. The hard block of the block copolymer includes less than 5 wt % and/or less than 4.5 wt % of ethylene, and optionally greater than 0.5 wt %, with a remainder of isotactic polypropylene that has a similar composition. For example, the hard block may include from 1.5 wt % to 4.1 wt % of ethylene and/or 2.1 wt % to 3.5 wt % of ethylene. Further, the block copolymer includes from 20 wt % to 50 wt % (e.g., 20 wt % to 40 wt %, 25 wt % to 35 wt %, and/or 28 wt % to 32 wt %) of the hard block, with the remainder being the soft block, based on the total weight of the block copolymer.

An iPP-EP block copolymer in the block composite polypropylene-based olefin block copolymer comprising iPP hard blocks and ethylene-propylene soft blocks offers a compatiblization solution to reduce the domain sizes (e.g., to be within the range of from 100 nm to 500 nm) of the elastomer phase (e.g., the modifier) when blended in a propylene polymer base. This may form compatibilized blends of polypropylene and elastomers offer a wider range of thermodynamically-stable compositions with morphologies finer than those achievable with classical blends, resulting in unique combinations of properties.

The melting temperature of the block composite may be from 110° C. to 130° C. (e.g., 115° C. to 125° C.). It is estimated that at a melting temperature of 110° C., the ethylene content in the hard block is approximately 4.0 wt %, and at 130° C., the ethylene content in the hard block is approximately 1.6 wt %. It is estimated that at a melting temperature of 115° C., the ethylene content in the hard block is approximately 3.4 wt %, and at 125° C., the ethylene content in the hard block is approximately 2.2 wt %. The overall ethylene content in the block composite may be from 25 wt % to 70 wt % (e.g., from 30 wt % to 60 wt %, from 35 wt % to 55 wt %, from 40 wt %, to 50 wt %, etc.), based on the total weight of the block composite.

Said in another way, the hard segment of the block copolymer refers to highly crystalline blocks of polymerized units in which a monomer (i.e., isotactic polypropylene) is present in an amount greater than 95 wt % and/or greater than 98 wt %. The soft segment includes from 50 wt % to 80 wt % of a comonomer (i.e., ethylene) and less than 50 wt % of the monomer (i.e., propylene). For example, soft segments refer to amorphous, substantially amorphous or elastomeric blocks of polymerized units in which the comonomer content is greater than 10 mol %. The weight percent of hard segments in the block copolymer may be from 5 wt % to 95 wt % (with the remainder being soft segments). The molecular weight of the block copolymer may be from 50,000 to 1,000,000 g/mol.

The block copolymer is characterized as having a block composite index equal to or greater than 0.1 and up to 1. For example, the block composite index may be from 0.1 to 0.9, from 0.1 to 0.8, from 0.1 to 0.7, from 0.1 to 0.6, from 0.1 to 0.5, from 0.1 to 0.4, from 0.1 to 0.3, from 0.1 to 0.2, etc. The block copolymer is characterized as having a molecular weight distribution, Mw/Mn, greater than about 1.3. For example the Mw/Mn may be from 1.4 to 5.0, from 1.7 to 3.5, and/or from 1.7 to 2.5.

The block composite may have a melt flow rate from 2 g/10 min to 100 g/10 min, according to ASTM D 1238 and at 230° C./2.16 kg. For example, melt flow rate may be from 2 g/10 min to 50 g/10 min, 2 g/10 min to 30 g/10 min, 2 g/10 min to 25 g/10 min, 2 g/10 min to 20 g/10 min, 2 g/10 min to 15 g/10 min, 3 g/10 min to 10 g/10 min, and/or 4 g/10 min to 7 g/10 min. The melt flow rate of the block composite may be less than the melt index (based on g/10 min according to ASTM D1238 and at 190° C./2.16 kg) of the polyolefin copolymer included in the modifier.

The block composite includes the block copolymers possessing a most probable distribution of block lengths. The block copolymers may contain 2 or 3 blocks or segments. In a process for making the polymers of the block composite, chain shuttling is used as a way to prolong the lifetime of a polymer chain such that a substantial fraction of the polymer chains exit at least the first reactor of a multiple reactor series or the first reactor zone in a multiple zoned reactor operating substantially under plug flow conditions in the form of polymer terminated with a chain shuttling agent, and the polymer chain experiences different polymerization conditions in the next reactor or polymerization zone. Different polymerization conditions in the respective reactors or zones include the use of different monomers, comonomers, or monomer/comonomer(s) ratio, different polymerization temperatures, pressures or partial pressures of various monomers, different catalysts, differing monomer gradients, or any other difference leading to formation of a distinguishable polymer segment. Thus, at least a portion of the polymer comprises two, three, or more, preferably two or three, differentiated polymer segments arranged intramolecularly.

The block composite polymers are prepared, e.g., by a process comprising contacting an addition polymerizable monomer or mixture of monomers under addition polymerization conditions with a composition comprising at least one addition polymerization catalyst, a cocatalyst, and a chain shuttling agent. The process is characterized by formation of at least some of the growing polymer chains under differentiated process conditions in two or more reactors operating under steady state polymerization conditions or in two or more zones of a reactor operating under plug flow polymerization conditions.

Suitable processes useful in producing the block composites may be found in, e.g. example, U.S. Pat. Nos. 8,053,529, 8,686,087, and 8,716,400. The polymerization may be carried out as a continuous polymerization, e.g., a continuous-solution polymerization, in which catalyst components, monomers, and optionally solvent, adjuvants, scavengers, and/or polymerization aids are continuously supplied to one or more reactors or zones and polymer product continuously removed therefrom. Within the scope of the terms "continuous" and "continuously" as used in this context are those processes in which there are intermittent additions of reactants and removal of products at small regular or irregular intervals, so that, over time, the overall process is substantially continuous. Further, a chain shuttling agent(s) may be added at any point during the polymerization including in a first reactor or zone, at the exit or slightly before the exit of the first reactor, between the first reactor or zone and a second or any subsequent reactor or zone, or even solely to the second or any subsequent reactor or zone. Exemplary chain shuttling agents, catalysts, and cocatalysts are those disclosed in, e.g., U.S. Pat. No. 7,951,882. For example, chain shuttling agents that are dialkyl zinc compounds may be used.

The catalyst may be prepared as a homogeneous composition by addition of the requisite metal complex or multiple complexes to a solvent in which the polymerization will be conducted or in a diluent compatible with the ultimate reaction mixture. The desired cocatalyst or activator and, optionally, the shuttling agent may be combined with the catalyst composition either prior to, simultaneously with, or after combination of the catalyst with the monomers to be polymerized and any additional reaction diluent.

Due to the difference in monomers, temperatures, pressures, or other differences in polymerization conditions between at least two of the reactors or zones connected in series, polymer segments of differing composition such as comonomer content, crystallinity, density, tacticity, regio-regularity, or other chemical or physical difference, within the same molecule are formed in the different reactors or zones. The size of each segment or block is determined by continuous polymer reaction conditions, and preferably is a most probable distribution of polymer sizes. Each reactor in the series can be operated under high pressure, solution, slurry, or gas phase polymerization conditions.

In the following exemplary processes, continuous or substantially continuous polymerization conditions may be employed. In a multiple zone polymerization, all zones operate under the same type of polymerization, such as solution, slurry, or gas phase, but at different process conditions. For a solution polymerization process, it is desirable to employ homogeneous dispersions of the catalyst components in a liquid diluent in which the polymer is soluble under the polymerization conditions employed. A high pressure process may be carried out at temperatures from 100° C. to 400° C. and at pressures above 500 bar (50 MPa). A slurry process may use an inert hydrocarbon diluent and temperatures of from 0° C. up to a temperature just below the temperature at which the resulting polymer becomes substantially soluble in the inert polymerization medium. Exemplary temperatures in a slurry polymerization are from 30° C. and pressures may range from atmospheric (100 kPa) to 500 psi (3.4 MPa).

Without limiting in any way the scope of the embodiments, one means for carrying out such a polymerization process is as follows. In one or more well stirred tank or loop reactors operating under solution polymerization conditions, the monomers to be polymerized are introduced continuously together with any solvent or diluent at one part of the reactor. The reactor contains a relatively homogeneous liquid phase composed substantially of monomers together with any solvent or diluent and dissolved polymer. Exemplary solvents include $C_{4-10}$ hydrocarbons or mixtures thereof, especially alkanes such as hexane or mixtures of alkanes, as well as one or more of the monomers employed in the polymerization. Catalyst along with cocatalyst and optionally chain shuttling agent are continuously or intermittently introduced in the reactor liquid phase or any recycled portion thereof at a minimum of one location.

The reactor temperature and pressure may be controlled by adjusting the solvent/monomer ratio, the catalyst addition rate, as well as by use of cooling or heating coils, jackets or both. The polymerization rate is controlled by the rate of catalyst addition. The content of a given monomer in the polymer product is influenced by the ratio of monomers in the reactor, which is controlled by manipulating the respective feed rates of these components to the reactor. The polymer product molecular weight is controlled, optionally, by controlling other polymerization variables such as the temperature, monomer concentration, or by the previously mentioned chain shuttling agent, or a chain terminating agent such as hydrogen. Connected to the discharge of the reactor, optionally by means of a conduit or other transfer means, is a second reactor, such that the reaction mixture prepared in the first reactor is discharged to the second reactor without substantially termination of polymer growth. Between the first and second reactors, a differential in at least one process condition is established. For example, use in formation of a copolymer of two or more monomers, the difference is the presence or absence of one or more comonomers or a difference in comonomer concentration. Additional reactors, each arranged in a manner similar to the second reactor in the series may be provided as well. Upon exiting the last reactor of the series, the effluent is contacted with a catalyst kill agent such as water, steam or an alcohol or with a coupling agent. The resulting polymer product is recovered by flashing off volatile components of the reaction mixture such as residual monomers or diluent at reduced pressure, and, if necessary, conducting further devolatilization in equipment such as a devolatilizing extruder.

Alternatively, the foregoing polymerization may be carried out in a plug flow reactor with a monomer, catalyst, shuttling agent, temperature or other gradient established between differing zones or regions thereof, optionally accompanied by separated addition of catalysts and/or chain shuttling agent, and operating under adiabatic or non-adiabatic polymerization conditions.

High Melt Flow Polyolefin Copolymer

In embodiments, the polyolefin copolymer is derived from ethylene and at least one of a $C_3$ to $C_{10}$ alpha-olefin or is derived from propylene and at least one of a $C_2$ and $C_4$ to $C_{10}$ alpha-olefin. For example, the polyolefin copolymer may be an ethylene-propylene copolymer, an ethylene-butylene copolymer, and/or an ethylene-octene copolymer. The polyolefin copolymer has a relatively high melt index such that the melt index is from 100 g/10 min to 2000 g/10 min, according to ASTM D1238 and at 190° C./2.16 kg. For example, the melt index may be from 100 g/10 min to 1500 g/10 min, 200 g/10 min to 1200 g/10 min, 300 g/10 min to 700 g/10 min, and/or 400 g/10 min to 600 g/10 min. The polyolefin copolymer has a relatively low density such that the density is from 0.860 g/cm$^3$ to 0.900 g/cm$^3$, according to ASTM D792. For example, the density may be from 0.860 g/cm$^3$ to 0.890 g/cm$^3$, 0.860 g/cm$^3$ to 0.885 g/cm$^3$, 0.865 g/cm$^3$ to 0.880 g/cm$^3$, 0.870 g/cm$^3$ to 0.879 g/cm$^3$, and/or 0.872 g/cm$^3$ to 0.876 g/cm$^3$.

The polyolefin copolymer may have a low glass transition temperature, e.g., less than −30° C., less than −40° C., and/or less than −50° C. The glass transition temperature ($T_g$) may be greater than −80° C. The Brookfield viscosity (@ 350° F./177° C.) may be from 1,000 cP to 25,000 cP (e.g., from 3000 cP to 20,000 cP, from 5000 cP to 20,000 cP, from 10,000 cP to 20,000 cP, and/or from 15,000 cP to 20,000 cP).

The polyolefin copolymer may have a low weight average molecular weight (Mw), e.g., less than or equal to 40,000 g/mole, less than or equal to 30,000 g/mole, and/or less than or equal to 25,000 g/mole. The weight average molecular weight (Mw) may be greater than or equal to 5000 g/mole, greater than or equal to 7000 g/mole, and/or greater than or equal to 10,000 g/mole.

Additional Polyolefin Copolymer

In embodiments, the additional copolymer, if present, may include a first additional copolymer and/or a second additional copolymer. The first additional copolymer has a refractive index from 1.490 to 1.510, as measured using a refractometer as would be understood by a person of ordinary skill in the art. The first additional copolymer may include a copolymer of at least two $C_2$ to $C_{10}$ alpha-olefins and/or a copolymer that is derived from at least styrene. The first additional copolymer may be a copolymer derived from at least two selected from (i.e., two or more of selected from the following list) ethylene, propylene, butylene, pentene, hexene, heptene, and octene, or may be a styrene based copolymer. For example, the first additional copolymer may be derived from at least two of ethylene, propylene, and butylene or is a styrene based copolymer. For example, the additional copolymer may include an ethylene-propylene copolymer and/or an ethylene-butylene copolymer. The second additional copolymer is miscible with polypropylene and is derived from propylene and at least one of ethylene and butene. For example, the second additional copolymer may be a propylene-ethylene interpolymer or a propylene-ethylene-butene interpolymer.

Exemplary additional copolymers derived from alpha-olefins are available from The Dow Chemical Company under the tradenames Engage™ and VERSIFY™ Exemplary styrene based copolymers from Kraton Performance Polymers under family designation Kraton®, such as the enhanced rubber segment Kraton® G1643M and Kraton® G1645M grades.

Propylene Polymer Base

The composition includes from 70 wt % to 88 wt % of the propylene polymer base that has a melt flow rate from 2 g/10 min to 100 g/10 min (e.g., from 10 g/10 min to 80 g/10 min, from 20 g/10 min to 60 g/10 min, from 30 g/10 min to 50 g/10 min, and/or from 35 g/10 min to 45 g/10 min), according to ASTM D 1238 and at 230° C./2.16 kg. The propylene polymer base may include one or more polypropylene based polymers that have a melt flow rate from 2 g/10 min to 100 g/10 min, according to ASTM D 1238 and at 230° C./2.16 kg. In exemplary embodiments, the composition may consist essentially of the modifier and the propylene polymer base. The propylene polymer base may include a random copolymer polypropylene that has an ethylene content from 0.5 wt % to 5.0 wt %, based on the total weight of the random copolymer polypropylene. The propylene polymer base may include 95 wt % to 100 wt % of the random copolymer polypropylene based on the total weight of the propylene polymer base.

The propylene polymer base may include polypropylene in the isotactic form of a homopolymer polypropylene and/or other forms of polypropylene can also be used (e.g., syndiotactic or atactic). The propylene polymer base may include an impact copolymer, which includes a rubber phase dispersed in propylene. The molecular weight and hence the melt flow rate of the polypropylene used may vary depending upon the application. A discussion of various polypropylene polymers is contained in, e.g., Modern Plastics Encyclopedia/89, mid October 1988 Issue, Volume 65, Number 11, pp. 86-92.

The propylene polymer base may include clarifying and/or nucleating agents therewithin. For example, clarifying and/or nucleating agents may alter the way polypropylene chains crystallize and agglomerate in a molten state. These agents may increase the onset of crystallization temperature. Clarifying agents (or clarifiers) are usually organic, non-polymeric molecules. The clarifying generally also may act as nucleating agents, but nucleating agents are not necessarily clarifying agents. Exemplary clarifiers are chemical derivatives of dibenzylidene sorbitol and have melting temperatures within the processing window of polypropylene resins. Nucleating agents generally are inorganic materials with a small average particle size and a high melting point. When a nucleated resin is melted in an extruder, the nucleating agent may typically remain solid and provide a site around which polypropylene spherulites can form. Exemplary nucleating agents are chemical derivatives of benzoic acid. For example, the nucleating agent may be sodium benzoate, kaolin, and/or talc.

The composition may be used in the manufacture of durable containers for applications requiring low temperature (such as sub-ambient and/or below 0° C.) mechanical. The containers may be suitable for use in food and beverage consumer markets. Exemplary container based applications that may benefit from the improved balance of impact, clarity, and modulus include food packaging (such as ice cream containers and puncture resistance bags) for low temperature mechanical properties, beverage bottles, and clear heavy duty shipping sacks.

EXAMPLES

Test Methods

Density is measured in accordance with ASTM D792. The result is reported in gamma (g) per cubic centimeter, or g/cm$^3$.

Melt Index ($I_2$) is measured in accordance with ASTM D-1238 (190° C.; 2.16 kg). The result is reported in grams/10 minutes.

Melt flow rate (MFR) is measured in accordance with ASTM D-1238 (230° C.; 2.16 kg). The result is reported in grams/10 minutes.

Tensile Properties, including tensile stress at break and tensile elongation at break, are measured according to ASTM D638.

Secant Flexural Modulus, including Flex 1% and Flex 2%, is measured according ASTM D790.

Percent Clarity, Percent Haze, and Percent Transmittance are measured using BYK Gardner Haze-gard as specified in ASTM D1746.

Izod Impact, including at 23° C., at 0° C., and −20° C., are measured according to ASTM D256, at a thickness as indicated in the respective examples. Samples are preparing by induction molding Differential Scanning calorimetry (DSC) is performed on a TA Instruments Q100 DSC V9.8 Build 296 using Universal V3.7A analysis software from TA Instruments. Samples are rapidly heated to 230° C. and held isothermally for 3 minutes in order to remove any previous heat history. The sample are then cooled to −90° C. at 10° C./minute cooling rate and held at −90° C. for 3 minutes. The first cooling and second heating curves are recorded. The percent crystallinity is calculated by dividing the heat of fusion ($H_f$), determined from the second heat curve, by a theoretical heat of fusion of 292 J/g for PE (165 J/g, for PP), and multiplying this quantity by 100 (for example, % cryst.=($H_f$/292 J/g)×100 (for PE)).

Unless otherwise stated, melting point(s) ($T_m$) of each polymer is determined from the second heat curve (peak Tm), and the crystallization temperature ($T_c$) is determined from the first cooling curve (peak Tc). With respect to DSC, the temperature at the maximum heat flow rate with respect to a linear baseline is used as the melting point. The linear baseline is constructed from the beginning of the melting (above the glass transition temperature) and to the end of the melting peak.

High Temperature Liquid Chromatography: High Temperature Liquid Chromatography Experimental Method Instrumentation is the HTLC experiment, which is done according to the published method with minor modifications (Lee, D.; Miller, M. D.; Meunier, D. M.; Lyons, J. W.; Bonner, J. M.; Pell, R. J.; Shan, C. L. P.; Huang, T. *J. Chromatogr. A* 2011, 1218, 7173). Two Shimadzu (Columbia, Md., USA) LC-20AD pumps are used to deliver decane and trichlorobenzene (TCB) respectively. Each pump is connected to a 10:1 fixed flow splitter (Part #: 620-PO20-HS, Analytical Scientific Instruments Inc., CA, USA). The splitter has a pressure drop of 1500 psi at 0.1 mL/min in $H_2O$ according to the manufacturer. The flow rates of both pumps are set at 0.115 mL/min. After the splitting, the minor flow is 0.01 mL/min for both decane and TCB, determined by weighing the collected solvents for more than 30 min. The volume of the collected eluent is determined by the mass and the densities of the solvents at room temperature. The minor flow is delivered to the HTLC column for separation. The main flow is sent back to the solvent reservoir. A 50-μL mixer (Shimadzu) is connected after the splitters to mix the solvents from Shimadzu pumps. The mixed solvents are then delivered to the injector in the oven of Waters (Milford, Mass., USA) GPCV2000. A Hypercarb™ column (2.1×100 mm, 5 μm particle size) is connected between the injector and a 10-port VICI valve (Houston, Tex., USA). The valve is equipped with two 60-μL sample loops. The valve is used to continuously sample eluent from the first dimension (D1) HTLC column to the second dimension (D2) SEC column. The pump of Waters GPCV2000 and a PLgel Rapid™-M column (10×100 mm, 5 μm particle size) are connected to the VICI valve for D2 size exclusion chromatography (SEC). The symmetric configuration is used for the connections as described in the literature (Brun, Y.; Foster, P. *J. Sep. Sci.* 2010, 33, 3501). A dual-angle light scattering detector (PD2040, Agilent, Santa Clara, Calif., USA) and an IR5 inferred absorbance detector are connected after the SEC column for measurement of concentration, composition, and molecular weight.

Separation for HTLC:

Approximately 30 mg are dissolved in 8-mL decane by gently shaking the vial at 160° C. for 2 hours. The decane contains 400 ppm BHT (2,6-Di-tert-butyl-4-methylphenol) as the radical scavenger. The sample vial is then transferred to the autosampler of GPCV2000 for injection. The temperatures of the autosampler, the injector, both the Hypercarb and the PLgel columns, the 10-port VICI valve, and both the LS and IR5 detectors are maintained at 140° C. throughout the separation.

The initial conditions before injection are as follows. The flow rate for the HTLC column is 0.01 mL/min. The solvent composition in the D1 Hypercarb column is 100% decane. The flow rate for the SEC column is 2.51 mL/min at room temperature. The solvent composition in the D2 PLgel column is 100% TCB. The solvent composition in the D2 SEC column does not change throughout the separation.

A 311-μL aliquot of sample solution is injected into the HTLC column. The injection triggers the gradient described below:

From 0-10 min, 100% decane/0% TCB;

From 10-651 min, TCB is increased linearly from 0% TCB to 80% TCB. The injection also triggers the collection of the light scattering signal at 15° angle (LS15) and the "measure" and "methyl" signals from IR5 detector ($IR_{measure}$ and $IR_{methyl}$) using EZChrom™ chromatography data system (Agilent). The analog and signals from detectors are converted to digital signals through a SS420X analog-to-digital converter. The collection frequency is 10 Hz. The injection also triggers the switch of the 10-port VICI valve. The switch of the valve is controlled by the relay signals from the SS420X converter. The valve is switched every 3 min. The chromatograms are collected from 0 to 651 min Each chromatogram consist of 651/3=217 SEC chromatograms.

After the gradient separation, 0.2 mL of TCB and 0.3 mL of decane are used to clean and re-equilibrate the HTLC column for next separation. The flow rate of this step is 0.2 mL/min, delivered by a Shimadzu LC-20 AB pump connected to the mixer.

Data Analysis for HTLC:

The 651 min raw chromatogram is first unfolded to give 217 SEC chromatograms. Each chromatogram is from 0 to 7.53 mL in the unit of 2D elution volume. The integration limit is then set and the SEC chromatograms undergo spike removal, baseline correction, and smoothing. The process is similar to batch analysis of multiple SEC chromatograms in conventional SEC. The sum of all the SEC chromatograms is inspected to ensure both left side (upper integration limit) and right side (lower integration limit) of the peak were at the baseline as zero. Otherwise, the integration limit is adjusted to repeat the process.

Each SEC chromatogram n from 1 to 217 yields an X-Y pair in the HTLC chromatogram, where n is the fraction number:

$X_n$=elution volume (mL)=D1 flow rate×n×$t_{switch}$
where $t_{switch}$=3 min is the switch time of the 10-port VICI valve.

$$Y_n = \text{signal intensity (Voltage)} = \sum_{peak\ start}^{peak\ end} IR_{measure,n}$$

The above equation uses $IR_{measure}$ signal as the example. The obtained HTLC chromatogram shows the concentrations of the separated polymeric components as a function of elution volume. The normalized $IR_{measure}$ HTLC chromatogram is shown in FIG. 9 with Y represented by dW/dV, meaning the normalized weight fractions with respect to the elution volume.

X-Y pairs of data are also obtained from $IR_{methyl}$ and LS15 signals. The ratio of $IR_{methyl}/IR_{measure}$ is used to calculate composition after calibration. The ratio of LS15/$IR_{measure}$ is used to calculate weight-average molecular weight ($M_w$) after calibration.

Calibration follows the procedures of Lee et al., ibid. High density polyethylene (HDPE), isotactic polypropylene (iPP), and ethylene-propylene copolymer with propylene contents of 20.0, 28.0, 50.0, 86.6, 92.0, and 95.8 wt % P are used as the standards for $IR_{methyl}/IR_{measure}$ calibration. The composition of the standards are determined by NMR. The standards are run by SEC with IR5 detector. The obtained $IR_{methyl}/IR_{measure}$ ratios of the standards are plotted as a function of their compositions, yielding the calibration curve.

The HDPE reference is used for routine LS15 calibration. The $M_w$ of the reference is predetermined by GPC as 104.2 kg/mol with LS and RI (refractive index) detectors. GPC uses NBS 1475 as the standard in GPC. The standard has a certified value of 52.0 kg/mol by NIST. Between 7 to 10 mg of the standard is dissolved in 8-mL decane at 160° C. The solution is injected to the HTLC column in 100% TCB. The polymer is eluted under constant 100% TCB at 0.01 mL/min. Therefore, the peak of the polymer appears at the HTLC column void volume. A calibration constant, n, is determined from the total LS15 signals ($A_{LS15}$) and the total $IR_{measure}$ signals ($A_{IR,measure}$):

$$\Omega = \frac{A_{LS15}}{A_{IR,measure} M_w}$$

The experimental LS15/$IR_{measure}$ ratio is then converted to $M_w$ through $\Omega$.

By way of example, three HTLC chromatograms are shown in FIG. 11. The black chromatogram is for Comparative BCN1 (i.e., CBCN1). The red chromatogram is for the blend of iPP and TAFMER™ P-0280 (an ethylene/alpha-olefin copolymer product available from Mitsui Chemicals). The blue chromatogram is for the blend of VERSIFY™ 2400 (a propylene-ethylene copolymer available from The Dow Chemical Company) and TAFMER™ P-0280. The dashed line is a linear regression fit of the chemical compositions of iPP, VERSIFY™ 2400, and TAFMER™ P-0280 versus their peak elution volumes. Note that VERSIFY™ 2400 has two peaks. The composition and elution volume of the main peak is used for the linear fit. The three polymers all have $M_w$ above 80,000 Daltons.

Transmission Electron Microscopy (TEM) is for morphology determination. Polymer films are prepared by compression molding followed by fast quenching. The polymer is pre-melted at 190° C. for 1 minute at 1000 psi and then pressed for 2 minutes at 5000 psi and then quenched between chilled platens (15-20° C.) for 2 minutes. The compression molded films are trimmed so that sections could be collected near the core of the films. The trimmed samples are cryopolished prior to staining by removing sections from the blocks at −60° C. to prevent smearing of the elastomer phases. The cryo-polished blocks are stained with the vapor phase of a 2% aqueous ruthenium tetraoxide solution for 3 hrs at ambient temperature. The staining solution is prepared by weighing 0.2 μm of ruthenium (III) chloride hydrate ($RuCl_3 \times H_2O$) into a glass bottle with a screw lid and adding 10 ml of 5.25% aqueous sodium hypochlorite to the jar. The samples are placed in the glass jar using a glass slide having double sided tape. The slide is placed in the bottle in order to suspend the blocks about 1 inch above the staining solution. Sections of approximately 90 nanometers in thickness are collected at ambient temperature using a diamond knife on a Leica EM UC6 microtome and placed on 600 mesh virgin TEM grids for observation.

Image Collection—

TEM images are collected on a JEOL JEM-1230 operated at 100 kV accelerating voltage and collected on a Gatan-791 and 794 digital cameras.

Xylene Soluble Fractionation Analysis: is performed by using a weighed amount of resin is dissolved in 200 ml o-xylene under reflux conditions for 2 hours. The solution is then cooled in a temperature controlled water bath to 25° C. to allow the crystallization of the xylene insoluble (XI) fraction. Once the solution is cooled and the insoluble fraction precipitates from the solution, the separation of the xylene soluble (XS) fraction from the xylene insoluble fraction is done by filtration through a filter paper. The remaining o-xylene solution is evaporated from the filtrate. Both XS and XI fractions are dried in a vacuum oven at 100° C. for 60 min and then weighed.

$^{13}$C Nuclear Magnetic Resonance (NMR) involves the following:

Sample Preparation:

The samples are prepared by adding approximately 2.7 g of a 50/50 mixture of tetrachloroethane-d2/orthodichlorobenzene that is 0.025M in chromium acetylacetonate (relaxation agent) to 0.21 g sample in a 10 mm NMR tube. The samples are dissolved and homogenized by heating the tube and its contents to 150° C.

Data Acquisition Parameters:

The data is collected using a Bruker 400 MHz spectrometer equipped with a Bruker Dual DUL high-temperature CryoProbe. The data is acquired using 320 transients per data file, a 7.3 sec pulse repetition delay (6 sec delay+1.3 sec acq. time), 90 degree flip angles, and inverse gated decoupling with a sample temperature of 125° C. All measurements are made on non spinning samples in locked mode.

Samples are homogenized immediately prior to insertion into the heated (130° C.) NMR Sample changer, and are allowed to thermally equilibrate in the probe for 15 minutes prior to data acquisition.

Gel Permeation Chromatography (GPC):

The gel permeation chromatographic system consists of either a Polymer Laboratories Model PL-210 or a Polymer Laboratories Model PL-220 instrument. The column and carousel compartments are operated at 140° C. Three Polymer Laboratories 10-micron Mixed-B columns are used. The solvent is 1,2,4 trichlorobenzene. The samples are prepared at a concentration of 0.1 grams of polymer in 50 milliliters of solvent containing 200 ppm of butylated hydroxytoluene (BHT). Samples are prepared by agitating lightly for 2 hours at 160° C. The injection volume used is 100 microliters and the flow rate is 1.0 ml/minute.

Calibration of the GPC column set is performed with 21 narrow molecular weight distribution polystyrene standards with molecular weights ranging from 580 to 8,400,000, arranged in 6 "cocktail" mixtures with at least a decade of separation between individual molecular weights. The standards are purchased from Polymer Laboratories (Shropshire, UK). The polystyrene standards are prepared at 0.025 grams in 50 milliliters of solvent for molecular weights equal to or greater than 1,000,000, and 0.05 grams in 50 milliliters of solvent for molecular weights less than 1,000,000. The polystyrene standards are dissolved at 80° C. with gentle agitation for 30 minutes. The narrow standards mixtures are run first and in order of decreasing highest molecular weight component to minimize degradation. The polystyrene standard peak molecular weights are converted to polyethylene molecular weights using the following equation (as described in Williams and Ward, *J. Polym. Sci., Polym. Let.*, 6, 621 (1968)): $M_{polypropylene} = 0.645 (M_{polystyrene})$.

Polypropylene equivalent molecular weight calculations are performed using Viscotek TriSEC software Version 3.0.

Preparation of Block Composite

A Block Composite is produced using a catalyst fed simultaneously into two reactors. The block composite includes (i) an ethylene-propylene polymer, (ii) an isotactic propylene polymer, and (iii) a block copolymer including an ethylene-propylene soft block that has a same composition as the ethylene-propylene polymer and an isotactic polypropylene hard block that as a same composition as the isotactic propylene polymer. With respect to the block copolymer, the ethylene-propylene soft block is produced in the first reactor and the isotactic propylene hard block is produced in the second reactor. The split between soft and hard block in the block copolymer is approximately 70/30.

The Block Composite is prepared using two continuous stirred tank reactors (CSTR) connected in series and using a catalyst fed simultaneously into both reactors. The soft block is produced in the first reactor and the hard block is produced in the second reactor. Each reactor is hydraulically full and set to operate at steady state conditions. In particular, the Block Composite is prepared by flowing monomers, Catalyst, Cocatalyst-1, Cocatalyst-2, and SA (as a chain shuttling agent) according to the process conditions outlined in Table 1, below. Two port injectors are used to feed the Catalyst, Cocatalyst-1, Cocatalyst-2, and SA (shuttling agent)-1, separately into the reactors. For preparation of the Block Composite, the Catalyst is ([[rel-2',2'''-[(1R,2R)-1,2-cylcohexanediylbis(methyleneoxy-κO)] bis[3-(9H-carbazol-9-yl)-5-methyl[1,1'-biphenyl]-2-olato-κO]](2-)]dimethylhafnium). The Cocatalyst-1 is a mixture of methyldi($C_{14-18}$ alkyl)ammonium salts of tetrakis(pentafluorophenyl)borate, prepared by reaction of a long chain trialkylamine (Armeen™ M2HT, available from Akzo-Nobel, Inc.) are used. The Cocatalyst-2 is mixed $C_{14-18}$ alkyldimethylammonium salt of bis(tris(pentafluorophenyl)-alumane)-2-undecylimidazolide, prepared according to U.S. Pat. No. 6,395,671, Ex. 16. The SA is a solution of diethylzinc (DEZ) that may contain 1-3 mol % of modified methylalumoxane (MMAO-3A) from Akzo Nobel Chemicals. Upon exiting the reactor, water and/or additives may be injected into the polymer solution.

The process conditions for producing the Block Composite are as follows:

TABLE 1

| Conditions | 1st Reactor | 2nd Reactor |
|---|---|---|
| Reactor Control Temp. (° C.) | 105.00 | 114.68 |
| Solvent Feed (lb/hr) | 284.83 | 174.76 |
| Propylene Feed (lb/hr) | 21.24 | 24.57 |
| Ethylene Feed (lb/hr) | 39.66 | 0.78 |
| Reactor Propylene Conc. (g/L) | 2.16 | 1.78 |
| Hydrogen Feed (SCCM) | 0 | 0 |
| Catalyst Flow (lb/hr) | 0.41 | 0.54 |
| Catalyst Conc. (ppm) | 199.96 | 199.96 |
| Cocatalyst-1 Flow (lb/hr) | 0.68 | 0.78 |
| Cocatalyst-1 Conc. (ppm) | 1399.37 | 1399.37 |
| Cocatalyst-2 Flow (lb/hr) | 1.47 | 0.39 |
| Cocatalyst-2 Conc. (ppm) | 1494.34 | 1494.34 |
| SA Flow (lb/hr) | 1.77 | 0 |
| SA Concentration (ppm) | 29986.88 | 0 |

The resultant Block Composite includes an ethylene-propylene (EP) polymer, an isotactic polypropylene (iPP) polymer, and an EP-iPP block copolymer. The DSC melting point temperature profile of the resultant Block Composite is shown in FIG. 1.

The characteristics of the Block Composite are shown in Table 2, below

TABLE 2

| | MFR (g/10 min at 230° C. and 2.1 kg) | Density (g/cm³) | wt % iPP from HTLC | Mw Kg/mol | Mw/Mn | Total C₂ (wt %) NMR | Tm (° C.)[1] | Tc (° C.) | Tg (° C.)[1] | Melt Enthalpy (J/g) |
|---|---|---|---|---|---|---|---|---|---|---|
| Block Composite | 5.2 | 0.874 | 10.1 | 144 | 2.36 | 47.2 | 121.6 | 69.4 | −48.6 | 37.8 |

The Block Composite has a Block Composite Index (BCI) of 0.175. The term BCI is herein defined to equal the weight percentage of the block copolymer divided by 100% (i.e. weight fraction). The value of the block composite index can range from 0 up to 1.0, whereas 1.0 would be equal to 100% of the block copolymer and zero would be for a material such as a traditional blend or random copolymer. Said in another way, for an insoluble fraction, the BCI is 1.000, and for a soluble fraction the BCI is assigned a value of zero.

In particular, the BCI is based on showing that insoluble fractions contain an appreciable amount of ethylene that would not otherwise be present if the polymer were simply a blend of iPP homopolymer and EP copolymer. To account for this "extra ethylene", a mass balance calculation can be performed to estimate a block composite index from the amount of xylene insoluble and soluble fractions and the weight % ethylene present in each of the fractions. To account for this "extra ethylene", a mass balance calculation can be performed to estimate a block composite index from an amount of xylene insoluble and soluble fractions and a weight % ethylene present in each of the fractions.

A summation of the weight % ethylene from each fraction according to Equation 1 results in an overall weight % ethylene (in the polymer). This mass balance equation can also be used to quantify the amount of each component in a binary blend or extended to a ternary, or n-component blend.

$$\text{Wt \% } C_{2_{Overall}} = w_{Insoluble}(\text{wt \% } C_{2_{Insoluble}}) + w_{soluble}(\text{wt \% } C_{2_{soluble}}) \quad \text{Eq. 1}$$

Applying equations 2 through 4, the amount of the soft block (providing the source of the extra ethylene) present in the insoluble fraction is calculated. By substituting the weight % $C_2$ of the insoluble fraction in the left hand side of equation 2, the weight % iPP hard and weight % EP soft can be calculated using equations 3 and 4. Note that the weight % of ethylene in the EP soft is set to be equal to the weight % ethylene in the xylene soluble fraction. The weight % ethylene in the iPP block is set to zero or if otherwise known from its DSC melting point or other composition measurement, the value can be put into its place.

$$\text{Wt \% } C_{2_{Overall \, or \, xylene \, insoluble}} = \quad \text{Eq. 2}$$
$$w_{iPPHard}(\text{wt \% } C_{2_{iPP}}) + w_{EPsoft}(\text{wt \% } C_{2_{EPsoft}})$$

$$w_{iPPhard} = \frac{\text{wt \% } C_{2_{overall \, or \, xylene \, insoluble}} - \text{wt \% } C_{2_{EPsoft}}}{\text{wt \% } C_{2_{iPPhard}} - \text{wt \% } C_{2_{EPsoft}}} \quad \text{Eq. 3}$$

$$w_{EPsoft} = 1 - w_{iPPHard} \quad \text{Eq. 4}$$

After accounting for the 'additional' ethylene present in the insoluble fraction, the only way to have an EP copolymer present in the insoluble fraction, the EP polymer chain must be connected to an iPP polymer block (or else it would have been extracted into the xylene soluble fraction). Thus, when the iPP block crystallizes, it may reduce the possibility of and/or prevent the EP block from solubilizing.

In particular, for the Block Composite used herein, the BCI is calculated as shown below in Table 3.

TABLE 3

| Line # | Variable | Source | Block Composite |
|---|---|---|---|
| 1 | Overall wt % C2 Total | Measured | 47.2 |
| 2 | wt % C2 in PP block/polymer | Measured | 2.7 |
| 3 | wt % C2 in EP block/polymer | Measured | 65.0 |
| 4 | wt fraction iPP (in block or polymer) | Calculated | 0.286 |
| 5 | wt fraction EP (in block or polymer) | Calculated | 0.714 |
| 6 | Analysis of HTLC Separation | — | |
| 7 | wt fraction xylene soluble | Measured | 0.589 |
| 8 | wt fraction xylene insoluble | Measured | 0.411 |
| 9 | wt % C2 in xylene insoluble | Measured | 21.7 |
| 10 | wt fraction PP in insoluble | Calculated | 0.695 |
| 11 | wt fraction EP in insoluble fraction | 1-Line 10 | 0.305 |
| 12 | wt fraction Diblock in insoluble fraction | Line 11/Line 5 | 0.427 |
| 13 | Block Composite Index (BCI) | Calculated | 0.175 |

To estimate the BCI, the relative amount of each block must be taken into account. To approximate this, the ratio between the EP soft and iPP hard is used. The ratio of the EP soft polymer and iPP hard polymer can be calculated using Equation 2 from the mass balance of the total ethylene measured in the polymer. Alternatively it could also be estimated from a mass balance of the monomer and comonomer consumption during the polymerization. The weight fraction of iPP hard and weight fraction of EP soft is calculated using Equation 2 and assumes the iPP hard contains no ethylene. The weight % ethylene of the EP soft is the amount of ethylene present in the xylene soluble fraction.

For example, if an iPP-EP polymer contains an overall of 47 wt % $C_2$ and is made under the conditions to produce an EP soft polymer with 67 wt % $C_2$ and an iPP homopolymer containing zero ethylene, the amount of EP soft and iPP hard is 70 wt % and 30 wt %, respectively. If the percent of EP is 70 wt % and the iPP is 30 wt %, the relative ratio of the EPDM:iPP blocks could be expressed as 2.33:1. Hence, if one skilled in the art, carries out a xylene extraction of the polymer and recovers 40 wt % insoluble and 60 wt % soluble, this would be an unexpected result and this would lead to the conclusion that a fraction of the block copolymer was present. If the ethylene content of the insoluble fraction is subsequently measured to be 25 wt % $C_2$, Equations 2 thru 4 can be solved to account for this additional ethylene and result in 37.3 wt % EP soft polymer and 62.7 wt % iPP hard polymer present in the insoluble fraction.

Depending on the estimations made of the total polymer composition and the error in the analytical measurements which are used to estimate the composition of the hard and soft blocks, between 5 to 10% relative error is possible in the computed value of the block composite index. Such estimations include the wt % C2 in the iPP hard block as measured from the DSC melting point, NMR analysis, or process conditions; the average wt % C2 in the soft block as estimated from the composition of the xylene solubles, or by NMR, or by DSC melting point of the soft block (if detected). But overall, the block composite index calculation reasonably accounts for the unexpected amount of 'additional' ethylene present in the insoluble fraction, the only way to have an EP copolymer present in the insoluble fraction, the EPDM polymer chain must be connected to an iPP polymer block (or else it would have been extracted into the xylene soluble fraction).

The Block Composite is further blended to prepare the Modifier, as discussed below.

Preparation of Modifiers

The modifiers are a blend of the Block Composite, a high melt flow polyolefin copolymer, and an additional copolymer having a refractive index substantially matched to that of polypropylene.

In particular, the materials principally used are the following:

| | |
|---|---|
| Block Composite | The Block Composite discussed above that includes block copolymers having 70 wt % of EP soft blocks (with 65 wt % of ethylene, based on the total weight of the EP block) and 30 wt % of iPP hard blocks. |
| Polyolefin Copolymer | A high melt flow ethylene-octene polyolefin elastomer having a melt index of 500 g/10 min (according to ASTM D1238 and at 190° C./2.16 kg), a density of 0.874 g/cm$^3$ (according to ASTM D792), a Brookfield Viscosity at 177° C. of 17,000 cps, a DSC melting point of 70° C., and glass transition temperature of −56° C. (available as AFFINITY ™ GA 1950 from The Dow Chemical Company). |
| Copolymer 1 | An ethylene-octene copolymer having a melt index of 30 (according to ASTM D1238 and at 190° C./2.16 kg), a density of 0.902 g/cm$^3$ (according to ASTM D792), a Mooney Viscosity of 2 MU (according to ASTM D1238 and at ML 1 + 4 @ 121° C.), a DSC melting point of 96° C., a glass transition temperature of −35° C., a haze of 45% (according to ASTM D1003), and a refractive index of approximately 1.508 (available as ENGAGE ™ 8402 from The Dow Chemical Company). |
| Copolymer 2 | A propylene-ethylene copolymer that is miscible in polypropylene having a melt flow rate of 8 g/10 min (according to ASTM D1238 and at 230° C./2.16 kg), a density of 0.863 g/cm$^3$ (according to ASTM D792), a haze of 3.1% (according to ASTM D1003) (at date of filing, commercially available as the developmental grade - Developmental DE 3401.05 - under the VERSIFY ™ family of products from The Dow Company, produced with a revolutionary catalyst in combination with Dow's proprietary INSITE ™ Technology and Solution Process, and available as a variation of VERSIFY ™ 3401). |

A First Modifier is prepared using 30 wt % of the Block Composite, 50 wt % of the Polyolefin Copolymer, and 20 wt % of the Copolymer 1, based on the total weight of the First Modifier. A Second Modifier is prepared using 30 wt % of the Block Composite, 50 wt % of the Polyolefin Copolymer, and 20 wt % of the Copolymer 2, based on the total weight of the Second Modifier.

In particular, the First and Second Modifiers are prepared by melt blending on a 25 mm, Coperion WP-25 ZSK, co-rotating, twin-screw extruder at a speed of 500 RPM. The components are fed into the extruder using individual loss/weight feeders. The antioxidant additive is tumble blended with the elastomer ahead of compounding. The compounding extruder rate is 0.38 kg/minute (50 lb/hour) with a melt temperature of about 220° C. (430° F.).

Preparation of Working Examples and Comparative Examples

For the Working Examples, one of the First Modifier and the Second Modifier is blending at varying weight percentages to form specimens at varying thicknesses. The Comparative Examples are prepared using benchmark polypropylene copolymers that have not been blended with either of the pre-formed First and Second Modifiers.

In particular, the materials principally used are the following:

| | |
|---|---|
| First Modifier | A modifier as discussed above that includes 30 wt % of the Block Composite, 50 wt % of the Polyolefin Copolymer, and 20 wt % of the Copolymer 1. |
| Second Modifier | A modifier as discussed above that includes 30 wt % of the Block Composite, 50 wt % of the Polyolefin Copolymer, and 20 wt % of the Copolymer 2. |
| RCPP | A clarified polypropylene random copolymer that is marketed as offering very good see-through and contact clarity, but is observed as having a relatively low toughness at lower temperatures, having a melt flow rate of 40 g/10 min (according to ASTM D1238 and at 230° C./2.16 kg), a density of 0.90 g/cm$^3$ (according to ASTM D792), and a haze of 8% (available as Pro-fax RP448S from LyondellBasell). |
| ICP | A polypropylene impact copolymer that is marketed as offering very good cold temperature impact resistance, but is observed as having a very low clarity, having a melt flow rate of 50 g/10 min (according to ASTM D1238 and at 230° C./2.16 kg) and a density of 0.90 g/cm$^3$ (according to ASTM D792) (available as Pro-fax EP348T from LyondellBasell). |
| Block Composite A | A block composite prepared similar to as discussed above, having having 50 wt % of EP soft blocks (with 88 wt % of ethylene, based on the total weight of the soft blocks) and 50 wt % of iPP hard blocks (with 12 wt % of ethylene, based on the total weight of the hard blocks), and a melt flow rate of 6 g/10 min at 230° C. and 2.1 kg. |

Working Examples 1 to 6 and Comparative Examples A to C are prepared according to the formulations in Table 4, below:

TABLE 4

| | Ex. 1 (wt %) | Ex. 2 (wt %) | Ex. 3 (wt %) | Ex. 4 (wt %) | Ex. 5 (wt %) | Ex. 6 (wt %) | Ex. A (wt %) | Ex. B (wt %) | Ex. C (wt %) |
|---|---|---|---|---|---|---|---|---|---|
| First Modifier | 15 | 20 | 25 | — | — | — | — | — | — |
| Second Modifier | — | — | — | 15 | 20 | 25 | — | — | — |
| RCPP | 85 | 80 | 75 | 85 | 80 | 75 | 100 | — | — |
| ICP | — | — | — | — | — | — | — | 100 | 85 |
| Block Composite A | — | — | — | — | — | — | — | — | 15 |

In particular, specimens for Working Examples 1 to 6 and Comparative Examples A to C are prepared by injection molding. In particular, the propylene base and modifier, according to the respective formulations, are dry-blended and injection molded on a KraussMaffei KM110-390 injection molding machine in B1470C, Lab 1 in Freeport. Single molds are used to make plaques (dimensions of 7.6 cm×7.6 cm×the corresponding sample thickness of 0.16 cm or 0.075 cm) and samples are cut from the plaques according to ASTM Tensile specimens used for IZOD, Flexural Modulus, and Tensile Testing.

The morphology of Comparative Examples B and C and Working Examples 1 to 3 are shown in respective FIGS. 2A to 2E. The morphology is shown with respect to both 5 μm and 1 μm. A significant improvement with respect to domain size for Working Examples 1 to 3 (FIGS. 2C to 2E) is seen in comparison to Comparative Examples B and C. Morphology is measured by TEM as discussed above.

The properties of Working Examples 1 to 6 and Comparative Examples A and B, at a plaque specimen thickness of 1.60 mm, are evaluated as shown below in Table 5.

With respect to Table 5 and Table 6, the flexural, optical testing and impact test specimens are cut from 7.6 cm×7.6 cm plaques. The properties are measured using the corresponding Test Methods discussed above.

What is claimed is:

1. A composition for forming a sub-ambient temperature use container, the composition comprising:
   from 12 wt % to 30 wt % of a modifier including:
   (a) from 20 wt % to 40 wt % of a block composite, based on a total weight of the modifier, the block composite including (i) an ethylene-propylene copolymer, (ii) an isotactic polypropylene polymer, and (iii) a block copolymer including an ethylene-pro-

TABLE 5

|  | Ex. 1 | Ex. 2 | Ex. 3 | Ex. 4 | Ex. 5 | Ex. 6 | Ex. A | Ex. B |
|---|---|---|---|---|---|---|---|---|
| Thickness (mm) | 1.60 | 1.60 | 1.60 | 1.60 | 1.60 | 1.60 | 1.60 | 1.60 |
| MFR (g/10 min at 230° C. and 2.1 kg) | 44 | 47 | 52 | 41 | 47 | 44 | 41 | 51 |
| Flex 1% Secant Modulus (ksi) | 158 | 136 | 124 | 92 | 83 | 81 | 201 | 181 |
| Flex 2% Secant Modulus (ksi) | 147 | 131 | 118 | 91 | 81 | 77 | 194 | 170 |
| Tensile Modulus at 2% (psi) | 93627 | 83744 | 78239 | 91901 | 79547 | 74764 | 126304 | 111167 |
| Tensile Stress @ break (psi) | 3608 | 3454 | 3341 | 3614 | 3482 | 3267 | 3702 | 2285 |
| % Tensile Elongation @ break | 444 | 444 | 443 | 444 | 444 | 444 | 444 | 28 |
| % Clarity | 99 | 99 | 99 | 99 | 99 | 99 | 99 | 7 |
| % Haze | 25 | 30 | 31 | 29 | 34 | 38 | 12 | 101 |
| % Transmittance | 83 | 82 | 80 | 80 | 78 | 76 | 88 | 66 |
| 23° C. Avg. Charpy Impact (kJ/m$^2$) | 30 | 33 | 30 | 33 | 33 | 33 | 5 | 8 |
| 23° C. Avg. Izod Impact (kJ/m$^2$) | 23 | 21 | 21 | 19 | 24 | 21 | 3 | 7 |
| 0° C. Avg. Izod Impact (kJ/m$^2$) | 8 | 24 | 28 | 10 | 25 | 25 | 1 | 7 |
| −20° C. Avg. Izod Impact (kJ/m$^2$) | 7 | 12 | 31 | 6 | 18 | 30 | 2 | 8 |

The properties of Working Examples 1 to 6 and Comparative Examples A and B, at a specimen thickness of 0.75 mm, are evaluated as shown below in Table 6.

TABLE 6

|  | Ex. 1 | Ex. 2 | Ex. 3 | Ex. 4 | Ex. 5 | Ex. 6 | Ex. A | Ex. B |
|---|---|---|---|---|---|---|---|---|
| Thickness (mm) | 0.75 | 0.75 | 0.75 | 0.75 | 0.75 | 0.75 | 0.75 | 0.75 |
| MFR (g/10 min at 230° C. and 2.1 kg) | 49 | 50 | 49 | 47 | 46 | 49 | 49 | 52 |
| Flex 1% Secant (ksi) | 155 | 164 | 136 | 178 | 142 | 111 | 259 | 154 |
| Flex 2% Secant (ksi) | 153 | 159 | 131 | 171 | 138 | 105 | 252 | 155 |
| Tensile Modulus at 2% (psi) | 89467 | 70527 | 64873 | 82749 | 67109 | 60999 | 128968 | 119152 |
| Tensile Stress @ break | 5091 | 4832 | 4636 | 5215 | 4963 | 4702 | 6126 | 2868 |
| Tensile Elongation @ break | 434 | 434 | 435 | 437 | 444 | 444 | 421 | 21 |
| % Clarity | 99 | 99 | 99 | 99 | 99 | 99 | 100 | 9 |
| % Haze | 9 | 11 | 11 | 11 | 13 | 16 | 4 | 101 |
| % Transmittance | 88 | 88 | 87 | 86 | 85 | 85 | 90 | 79 |
| 23° C. Avg. Charpy Impact (kJ/m$^2$) | 30 | 30 | 30 | 30 | 30 | 30 | 30 | 30 |
| 23° C. Avg. Izod Impact (kJ/m$^2$) | 9 | 13 | 12 | 9 | 13 | 8 | 3 | 26 |
| 0° C. Avg. Izod Impact (kJ/m$^2$) | 11 | 11 | 10 | 9 | 8 | 8 | 2 | 18 |
| −20° C. Avg. Izod Impact (kJ/m$^2$) | 7 | 9 | 9 | 6 | 8 | 11 | 1 | 14 | pylene soft block that has a same composition as the ethylene-propylene polymer and an isotactic polypropylene hard block that has a same composition as the isotactic polypropylene polymer, the soft block comprising from 50 wt % to 80 wt % of ethylene based on a total weight of the soft block, and the block copolymer including from 20 wt % to 50 wt % of the hard block, based on the total weight of the block copolymer, (b) from 40 wt % to 60 wt % of a polyolefin copolymer, based on a total weight of the modifier, the polyolefin copolymer being derived from ethylene and at least one of a $C_3$ to $C_{10}$ alpha-olefin, and the polyolefin copolymer having a melt index from 100 g/10 min to 1500 g/10 min, according to ASTM D1238 and at 190° C./2.16 kg, and a density from 0.860 g/cm$^3$ to 0.900 g/cm$^3$, and (c) optionally, from 0 wt % to 30 wt % of at least one of a first additional copolymer that has a refractive index from 1.490 to 1.510 and a second additional copolymer that is miscible with polypropylene, which second additional copolymer is derived from propylene and at least one of ethylene and butene; and from 70 wt % to 88 wt % of a propylene polymer base that has a melt flow rate from 2 g/10 min to 100 g/10 min, according to ASTM D 1238 and at 230° C./2.16 kg.

2. The composition as claimed in claim 1, wherein the propylene polymer base includes a random copolymer polypropylene that has an ethylene content from 0.5 wt % to 5.0 wt %, based on the total weight of the random copolymer polypropylene.

3. The composition as claimed in claim 1, wherein the block composite has a melt flow rate from 2 g/10 min to 100 g/10 min, according to ASTM D 1238 and at 230° C./2.16 kg.

4. The composition as claimed in claim 1, wherein the block composite, the polyolefin copolymer, and optionally the additional copolymer of the modifier are provided in pre-blended form prior to blending the modifier with the propylene polymer base, the composition including the modifier finely dispersed in the polypropylene polymer.

5. The composition as claimed in claim 1, wherein the first additional copolymer is present in an amount from 10 wt % to 30 wt %, the block composite is present in an amount from 25 wt % to 35 wt %, and the polyolefin elastomer is present in an amount from 45 wt % to 55 wt %.

6. The composition as claimed in claim 5, wherein the first additional copolymer is a copolymer derived from at least two selected from ethylene, propylene, butylene, pentene, hexene, heptene, and octene, or the first additional copolymer is a styrene based copolymer.

7. The composition as claimed in claim 1, wherein the polyolefin elastomer is derived from octene.

8. The composition as claimed in claim 1, wherein the modifier is present in an amount greater than 15 wt %.

9. A freezer container formed from the composition as claimed in claim 1, wherein a film formed from the composition has greater than 98% clarity, an Izod impact greater than 5 kJ/m$^2$ at −20° C., according to ASTM D256, at a thickness of less than 3.0 mm.

10. A method of manufacturing a sub-ambient temperature use container, the method comprising:

providing a modifier that is a blend of:

(a) from 20 wt % to 40 wt % of a block copolymer, based on a total weight of the modifier, the block copolymer including an isotactic polypropylene hard block and an ethylene-propylene soft block, the soft block comprising from 50 wt % to 80 wt % of ethylene based on a total weight of the soft block, and the block copolymer including from 20 wt % to 50 wt % of the hard block, based on the total weight of the hard block, (b) from 40 wt % to 60 wt % of a polyolefin elastomer, based on a total weight of the modifier, the polyolefin elastomer having a melt index from 100 g/10 min to 1500 g/10 min, according to ASTM D1238 and at 190° C./2.16 kg, and a density from 0.860 g/cm$^3$ to 0.900 g/cm$^3$, the polyolefin elastomer being derived from at least one $C_3$ to $C_{10}$ alpha-olefin, and (c) from 0 wt % to 30 wt % of an optional copolymer that as a refractive index from 1.490 to 1.510; and blending from 12 wt % to 30 wt % of the modifier with 70 wt % to 88 wt % of a propylene polymer base, the propylene polymer base having a melt flow rate from 2 g/10 min to 100 g/10 min, according to ASTM D 1238 and at 230° C./2.16 kg.

* * * * *